(12) United States Patent
Williams et al.

(10) Patent No.: US 10,371,607 B2
(45) Date of Patent: Aug. 6, 2019

(54) TAMPER-RESISTANT CHEMICAL SAMPLING

(71) Applicant: Battelle Memorial Institute, Columbus, OH (US)

(72) Inventors: Pax T. Williams, Kennett Square, PA (US); David C. Seibert, Jr., Colora, MD (US); Edward J. Sullivan, Lewis Center, OH (US); Thomas S. O'Donnell, Arlington, VA (US)

(73) Assignee: BETTELLE MEMORIAL INSTITUTE, Columbus, OH (US)

( * ) Notice: Subject to any disclaimer, the term of this patent is extended or adjusted under 35 U.S.C. 154(b) by 160 days.

(21) Appl. No.: 15/321,831

(22) PCT Filed: Jun. 24, 2015

(86) PCT No.: PCT/US2015/037423
§ 371 (c)(1),
(2) Date: Dec. 23, 2016

(87) PCT Pub. No.: WO2015/200485
PCT Pub. Date: Dec. 30, 2015

(65) Prior Publication Data
US 2017/0131186 A1    May 11, 2017

Related U.S. Application Data

(60) Provisional application No. 62/016,739, filed on Jun. 25, 2014.

(51) Int. Cl.
*G01N 1/22* (2006.01)
*B01L 3/00* (2006.01)
(Continued)

(52) U.S. Cl.
CPC ............ *G01N 1/2273* (2013.01); *B01L 3/508* (2013.01); *G01N 1/2214* (2013.01);
(Continued)

(58) Field of Classification Search
CPC ............... G01N 1/2273; G01N 1/2214; G01N 2001/021; G01N 2001/007;
(Continued)

(56) References Cited

U.S. PATENT DOCUMENTS 4,376,489 A * 3/1983 Clemens .............. B65D 88/128
137/264
4,460,106 A * 7/1984 Moulding, Jr. .... B65D 83/0409
221/1
(Continued)

FOREIGN PATENT DOCUMENTS

| DE | 102005040872 B3 | 4/2007 |
|---|---|---|
| WO | 0019195 A1 | 4/2000 |
| WO | 2008155532 A2 | 12/2008 |

OTHER PUBLICATIONS

Chai, Meng et al. "Analysis of environmental air samples by solid-phase microextraction and gas chromatography/ion trap mass spectrometry." Environmental Science and Technology (1995) 29 693-701 (Year: 1995).*

*Primary Examiner* — Christopher Adam Hixson
(74) *Attorney, Agent, or Firm* — Benesch, Friedlander, Coplan & Aronoff LLP

(57) ABSTRACT

Methods, systems, and apparatuses are disclosed for a tamper-resistant collection and retention a chemical sample. In one embodiment, the tamper-resistant system comprises a container operable to collect and retain a chemical sample, a tamper-resistant mechanism operable to disengage at a first chemical sample to allow for a collection of a chemical sample, wherein the tamper-resistant mechanism is operable to record one or more of: a date, a time, and a location, of (Continued)

the chemical sample during the collection of the chemical sample, and wherein the tamper-resistant mechanism is further operable to re-engage and lock after the collection of the chemical sample to resist subsequent chemical samples after the first chemical sampling.

17 Claims, 9 Drawing Sheets

(51) Int. Cl.
G01N 1/00 (2006.01)
G01N 1/02 (2006.01)
(52) U.S. Cl.
CPC ... *B01L 2200/082* (2013.01); *B01L 2200/141* (2013.01); *B01L 2300/023* (2013.01); *B01L 2300/024* (2013.01); *B01L 2300/025* (2013.01); *B01L 2300/069* (2013.01); *B01L 2300/16* (2013.01); *G01N 2001/007* (2013.01); *G01N 2001/021* (2013.01); *G01N 2001/027* (2013.01)

(58) Field of Classification Search
CPC ............... G01N 2001/027; B01L 3/508; B01L 2200/082; B01L 2200/141; B01L 2300/069; B01L 2300/025; B01L 2300/024; B01L 2300/023; B01L 2300/16
See application file for complete search history.

(56) References Cited

U.S. PATENT DOCUMENTS

| 6,929,778 | B2* | 8/2005 | Nunes | B01L 9/54 422/430 |
|---|---|---|---|---|
| 2004/0043443 | A1 | 3/2004 | Legeune | |
| 2005/0022581 | A1* | 2/2005 | Sunshine | G01N 29/022 73/31.05 |
| 2007/0295112 | A1 | 12/2007 | Freeman | |
| 2009/0266786 | A1* | 10/2009 | Sasaki | B65D 1/0223 215/384 |
| 2013/0126530 | A1* | 5/2013 | Morris, Jr. | B65D 50/046 220/288 |

* cited by examiner

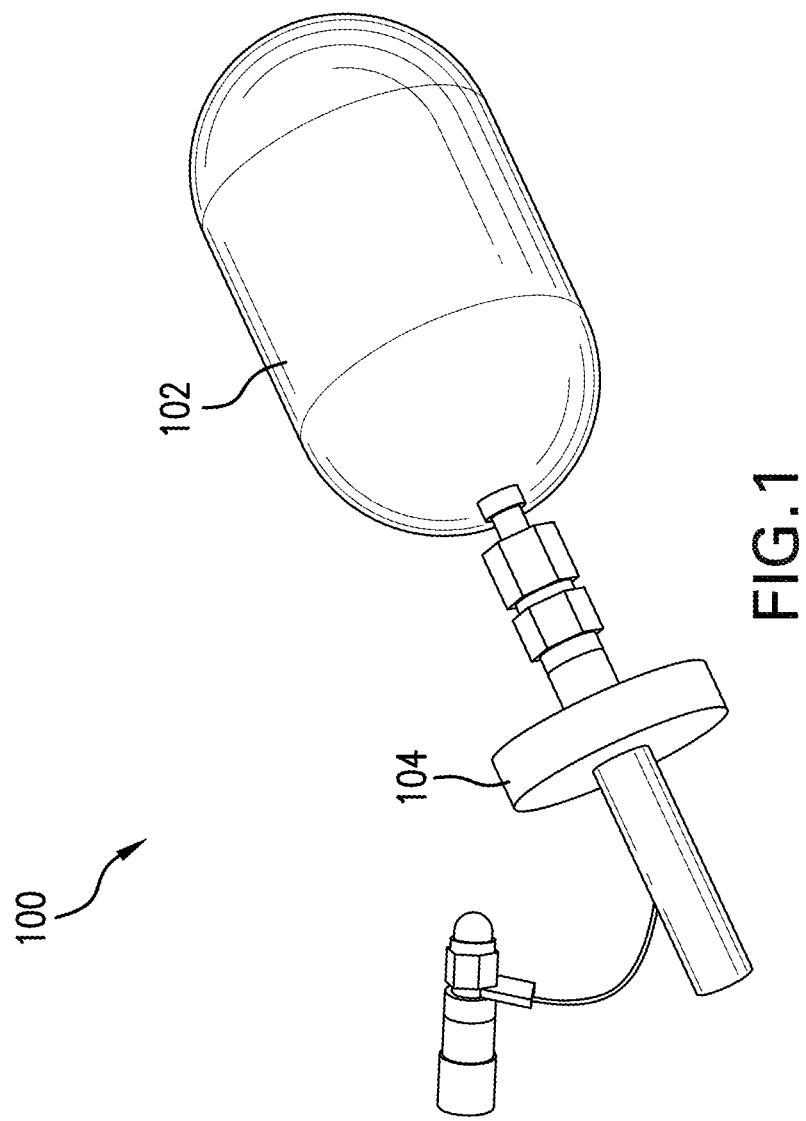

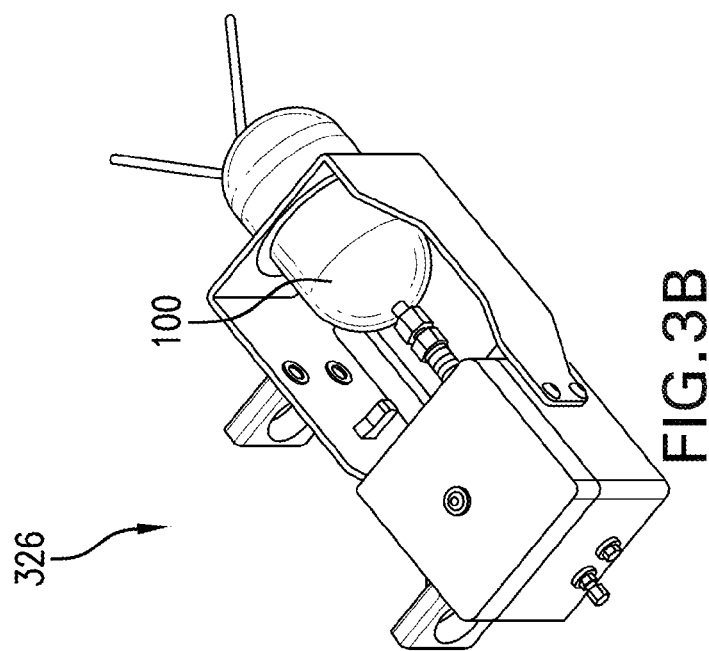
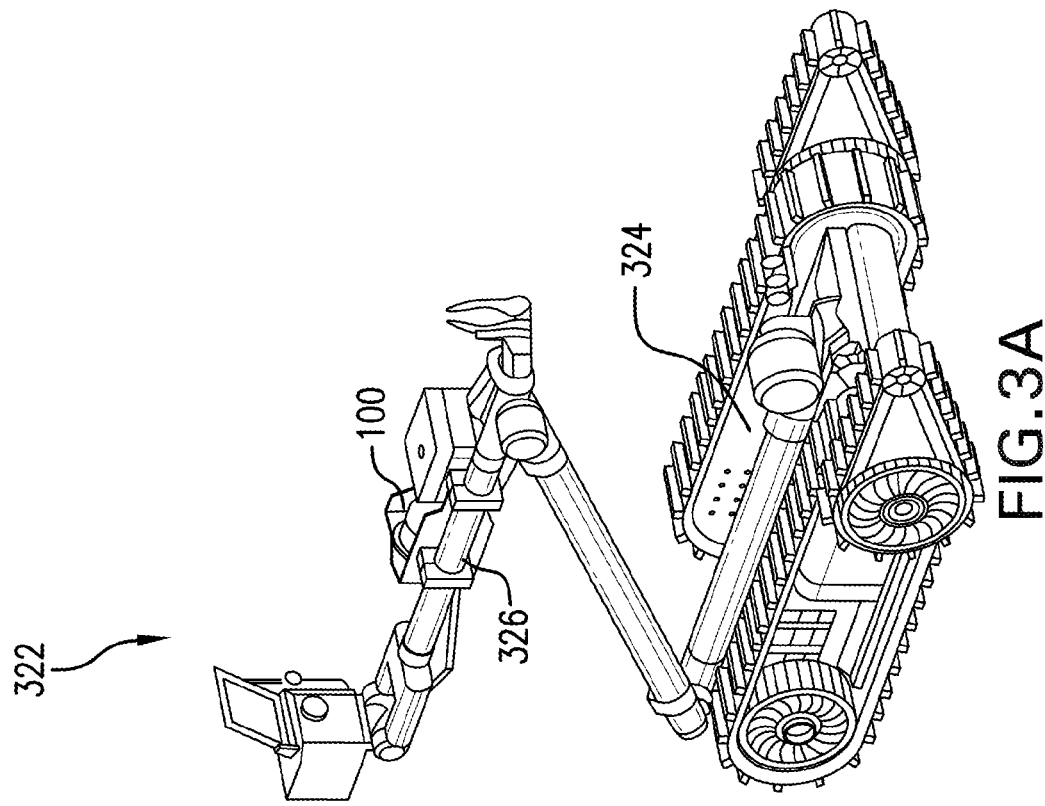

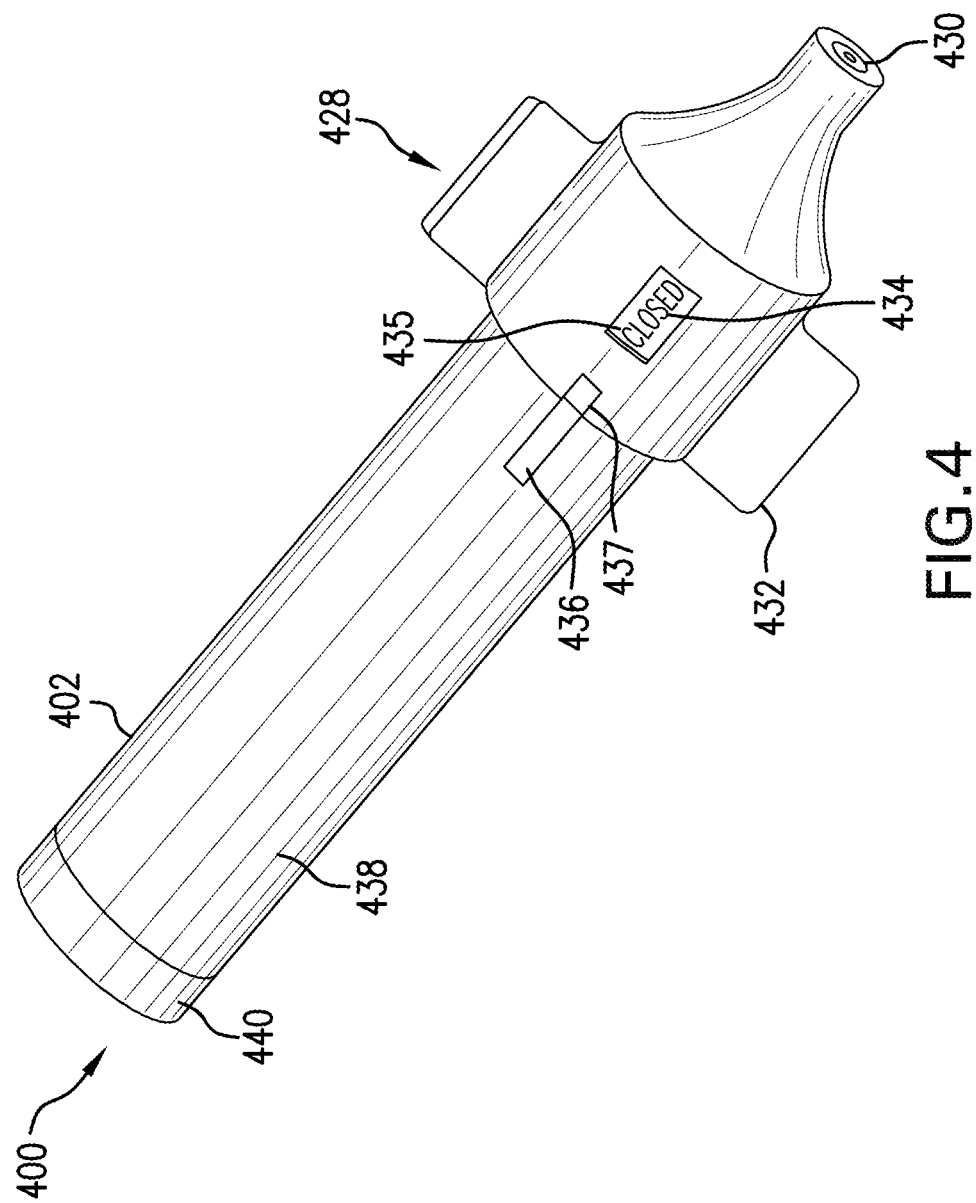

1000

Removing tamper-resistant chemical sampling apparatus from protective packaging (1001)

Turning twist mechanism to an open position to allow a chemical sample to be collected (1003)

Leaving twist mechanism in an open position for at least 5 seconds during a chemical sample (1005)

Turning twist mechanism to a closed position after collecting a chemical sample to retain chemical sample within tamper-resistant chemical sampling apparatus (1007)

Locking twist mechanism in a locked position (1009)

Examining a GPS indicator light to determine successful acquisition of GPS satellite signal and recordation of GPS coordinate (1011)

Placing tamper-resistant chemical sampling apparatus back into packaging and sealing packaging (1013)

FIG. 10

TAMPER-RESISTANT CHEMICAL SAMPLING

CROSS-REFERENCE TO RELATED APPLICATIONS

This application is a national stage filing under 35 U.S.C. § 371 of PCT/US15/37423, filed Jun. 24, 2015, which claims priority from U.S. Provisional Pat. App. No. 62/016,739 filed on Jun. 25, 2014. Each of the above-referenced applications is incorporated by reference herein in its entirety.

BACKGROUND

Chemical Warfare Agents (CWAs), commonly known as chemical weapons, are a class of weapons of mass destruction (WMD) designed to kill and harm large numbers of victims. Unlike conventional weapons that rely on explosive force, CWAs rely on the toxicity of chemical components to harm humans, agriculture, and livestock. While nations have long endeavored to reduce and eliminate CWAs, the production, stockpiling, and use of CWAs continues.

Efforts to curb the production and proliferation of CWAs through treaties such as the Chemical Weapons Convention (CWC) have led to the destruction and reduced availability of CWA stockpiles throughout the world. In response, terrorists or other wrongdoers may improvise with Toxic Industrial Chemicals (TICs) for use in chemical attacks.

Unlike CWAs, TICs are not intended for use as weapons. TICs may be employed for beneficial purposes and may have everyday use in many industrial processes. Nevertheless, exposure to significant amounts of TICs may cause injury or death. Additionally, industrial accidents may cause the release of TICs, which may injure or kill workers, first responders, and members of the public.

Chemical sampling may be used to identify CWAs and TICs. Typically, a sample from an area known or suspected to be affected by CWAs and TICs may be taken and stored in a container such as a passivated canister. The container may be transported to a laboratory or another facility for analysis of the sample. The sample may be extracted from the container and analyzed with an analytical instrument such as a gas chromatograph-mass spectrometer (GC-MS) to determine the presence of CWAs, TICs, or both.

The present application appreciates that collection, retention, custody, and control of a chemical sample may be a challenging endeavor.

SUMMARY

Systems, methods, and apparatuses are provided for effective, tamper-resistant collection and retention of a chemical sample.

In one embodiment, a tamper-resistant system for chemical sampling is provided. The system may include a container. The container may be operable to collect and retain a chemical sample. The system may include a tamper-resistant mechanism. The tamper-resistant mechanism may be operable to disengage at a first chemical sampling event to allow collection of a chemical sample after disengagement. The tamper-resistant mechanism may be operable to record one or more of: a collection date, a collection time, and a collection location of the chemical sample. The tamper-resistant mechanism may be operable to re-engage and lock to resist subsequent chemical sampling events after the first chemical sampling.

In another embodiment, a tamper-resistant apparatus for chemical sampling is provided. The apparatus may include (1) a stainless steel canister for retaining a chemical sample. The stainless steel canister may include an outer surface and an inner surface. The outer surface may include a surface treatment to provide one or more of: an increased friction between the outer surface and another surface and a markable surface to accept and retain a marking. The inner surface may be passivated effective to reduce a chemical reactivity between the stainless steel canister and the chemical sample.

The apparatus may also include (2) a tamper-resistant mechanism. The tamper-resistant mechanism may be operable to one or more of: collect the chemical sample, retain the chemical sample, and render the chemical sample tamper-resistant. The tamper-resistant mechanism may include a slide lock. The slide lock may be operable to resist rotation of a twist mechanism. The tamper-resistant mechanism may include the twist mechanism. The twist mechanism may be operable to rotate from a closed position to an open position. The open position of the twist mechanism may be effective to permit passage of the chemical sample into an interior of the stainless steel canister through a calibrated orifice. The tamper-resistant mechanism may include an electronic device operable to generate a first DTG data associated with a collection time of the chemical sample. The tamper-resistant mechanism may include a GPS device. The GPS device may be operable to acquire a GPS satellite signal and generate a global coordinate data associated with a location of the chemical sample. The GPS device may be operable to assign and record a second DTG data associated with an acquisition time of the GPS satellite signal by the GPS. The GPS device may be operable to record one or more attempt DTG data associated with a time for each attempt by the GPS device to acquire the GPS satellite signal. The tamper-resistant mechanism may include a temperature sensor to sense and record temperature data from the interior of the stainless steel canister. The tamper-resistant mechanism may include a memory. The memory may be operable to store one or more of the first DTG data, the global coordinate data, the second DTG data, the attempt DTG data, chemical data associated with a chemical sample detected by a chemical detector on a chip, the temperature data, and a fault code; an RFID device operable to wirelessly transfer the first DTG data, the global coordinate data, the second DTG data, the attempt DTG data, the chemical data, the temperature data, and the fault code, stored on the memory to a laboratory interface. The apparatus may also include (3) an extractor operatively connected to the calibrated orifice. The extractor may be operable to extract one or more analytes from the chemical sample for analysis. The extractor may include one or more of: a SPME fiber, a glass tube, a chemical detector on chip, a polymer, and a sorbent.

In another embodiment, a method of chemical sampling using a tamper-resistant chemical sampling apparatus is provided. The method may include removing the tamper-resistant chemical sampling apparatus from a packaging. The method may include turning a twist mechanism on the tamper-resistant chemical sampling apparatus to an open position effective to allow a chemical sample to be collected into the tamper-resistant chemical sampling apparatus through a calibrated orifice. The method may include leaving the twist mechanism in the open position for a period of time effective to collect the chemical sample through the calibrated orifice and into the tamper-resistant chemical sampling apparatus. The method may include turning the twist mechanism on the tamper-resistant chemical sampling apparatus to a closed position after collecting the chemical sample to retain the chemical sample within the tamper-resistant chemical sampling apparatus. The method may include locking the twist mechanism into a locked position to resist the twist mechanism from turning. The method may include examining GPS indicator lights after closing and locking the twist mechanism to determine acquisition of a GPS satellite signal and recordation of a GPS coordinate. The method may include sealing the tamper-resistant chemical sampling apparatus back into the packaging.

BRIEF DESCRIPTION OF THE DRAWINGS

The accompanying figures, which are incorporated in and constitute a part of the specification, illustrate various example systems, methods, and results, and are used merely to illustrate various example embodiments.

FIG. 1 illustrates an example chemical sampling container.

FIG. 3A illustrates an example chemical sampling system.
FIG. 3B illustrates an example chemical sampling system.
FIG. 4 illustrates an example tamper-resistant chemical sampling system.
FIG. 10 is a flow chart of an example method for tamper-resistant chemical sampling.

DETAILED DESCRIPTION

Embodiments claimed herein disclose methods, systems, and apparatuses for a tamper-resistant collection, retention, custody, and control of a chemical sample.

FIGS. 1, 2A, 2B, 3A, and 3B illustrate systems and apparatuses for chemical sampling. For example, FIG. 1 illustrates a chemical sample apparatus 100. Chemical sample apparatus 100 may include a canister 102, e.g., for storing a chemical sample. Chemical sample apparatus 100 may include a valve 104, e.g., to control a passage of a chemical sample into and out of canister 102.

Figure 2B:
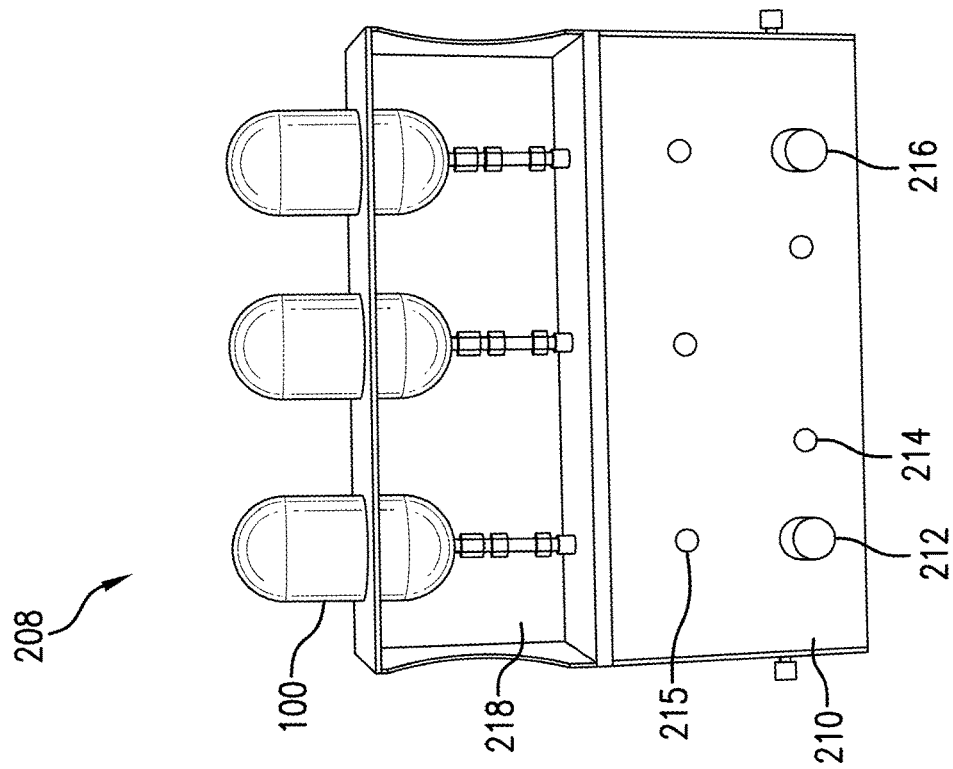
FIG. 2B illustrates an example chemical sampling system.
Figure 2A:
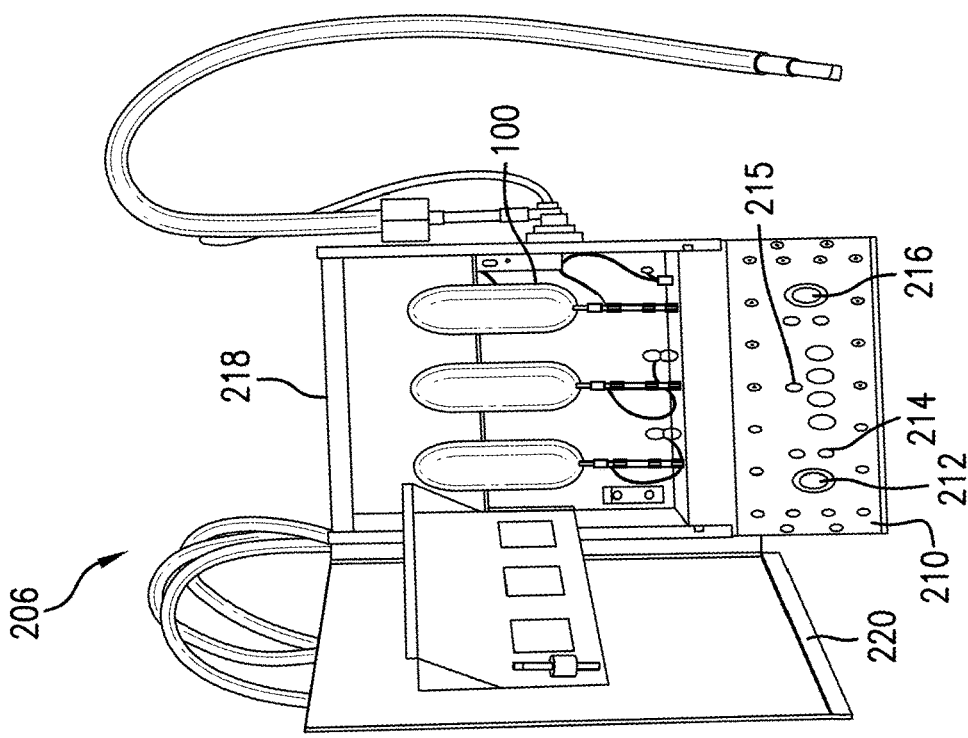
FIG. 2A illustrates an example chemical sampling system.

FIGS. 2A and 2B illustrate mounting platforms 206 and 208 that may be used in conjunction with one or more chemical sample apparatuses 100. With reference to FIG. 2A, mounting platform 206 may be mounted to a vehicle. Chemical sample apparatuses 100 may be reversibly mounted to a housing 218 of vehicle mounting platform 206, e.g., to be secured to housing 218 in various orientations. Vehicle mounting platform 206 may include a control interface 210 for semi-automatic chemical sampling. Control interface 210 may include hardware 212 to initiate a chemical sampling event. Hardware 212 may include a button, switch, and the like. Actuation of hardware 212 may initiate a chemical sampling event. Control interface 210 may further include one or more indicators, such as light 214, e.g., to provide a visual indication that vehicle mounting platform 206 is powered, operable, and the like. One or more indicators such as lights 215 may be provided on control interface 210 to provide a user with a status indication of chemical sample apparatus 100 on vehicle mounting platform 206. Hardware 216 may be actuated to reset alone or more, e.g., all, control functions on control interface 210. Vehicle mounting platform 206 may include door 220. Door 220 may be used, e.g., to enclose chemical sample apparatuses 100 within housing 218, e.g., to restrict access to chemical sample apparatus 100. For example, door 220 may lock to restrict access to chemical sample apparatus 100.

Referring to FIG. 2B, mounting platform 208 may be mounted to or within a fixed location, such as a building, a bridge, a tunnel, and the like. Building mounting platform 208 may be operated similarly to vehicle mounting platform 206.

FIG. 3A illustrates a robotic mounting platform 322. Chemical sample apparatus 100 may be adapted to be mounted on a remote controlled or robotic device 324. Robotic device 324 may include carriage 326 to mount chemical sample apparatus 100 to robotic device 324. As shown in FIG. 3B, carriage 326 may be used, e.g., to position chemical sample apparatus 100 in a suitable chemical sampling position. Carriage 326 may fixedly retain chemical sample apparatus 100, e.g., for use in rugged terrain and conditions. Carriage 326 may provide selective removability of each chemical sample apparatus 100 from carriage 326.

FIG. 4 illustrates an example tamper-resistant chemical sampling apparatus 400. Tamper-resistant chemical sampling apparatus 400 may include, for example, one or more of: a container portion 402, a valve mechanism 428, a calibrated orifice 430, and a GPS device 440. Container portion 402 may be operable to collect and retain a chemical sample. Valve mechanism 428 may be operatively connected, e.g., to one or both of calibrated orifice 430 and container portion 402. Valve mechanism 428 may be operable to control a flow of a chemical sample, e.g., through calibrated orifice 430 into container portion 402.

In various embodiments, container portion 402 may be a passivated stainless steel canister for collecting and retaining a chemical sample. Container portion 402 may include any durable, rugged material such as a metal, ceramic, glass, a polymeric material, plastic, combinations thereof, and the like. For example, container portion 402 may include a material rugged enough to withstand a drop from at least about 6.5 feet (about 2 meters) in height without affecting desired operational characteristics of container portion 402, such as retention of a chemical sample and operation of tamper-resistant chemical sampling apparatus 400. For example, container 402 may be operable to withstand a drop shock sustained from a fall of at least about 2 meters corresponding to an impact shock between container 402 and a concrete ground surface with, e.g., a compressive force of greater than 15 MPa. For example, container 402 may resist breakage, e.g., being operable to retain a previously collected chemical sample. Further, for example, after such a drop shock, container 402 may remain operable to collect a chemical sample. Further, for example, container portion 402 may be capable of withstanding repeated drops at heights of at least about 6.5 feet (about 2 meters) without affecting operation of tamper-resistant chemical sampling apparatus 400.

In various embodiments, container portion 402 may include a nonreactive material configured to resist reaction with a collected chemical sample and/or resist tainting the collected chemical sample. Further, for example, an interior of container portion 402 may be passivated with a coating or manufacturing process to resist unwanted reactions from occurring between a material of container portion 402 and a chemical sample contained therein.

In some examples, an exterior surface 438 of container portion 402 may be treated with a surface treatment, e.g., to increase a friction of exterior surface 438 to provide an increased friction between exterior surface 438 and another surface, e.g. with a glove surface for gripping. For example, exterior surface 438 may include a friction coating to assist and/or increase a user's grip of tamper-resistant chemical sampling apparatus 400, e.g., to resist slippage during chemical sampling. Further, for example, a surface treatment of exterior surface 438 may permit a user to write on exterior surface 438 of tamper-resistant chemical sampling apparatus 400 with one or more of: an inked-based marking, a pigment based marking, a paint-based marking, a graphite or charcoal-based marking, a wax-based marking, an abrasive, e.g., engraving-based marking, an impact based marking, and the like. For example, a surface treatment may provide for a variety of mineral-based or chemical-based writing instruments to mark exterior surface 438. A surface treatment that provides for marking of exterior surface 438 may be further operable to retain the mark on exterior surface 438. A surface treatment may allow for an abrasive, e.g., scratching instrument or engraving instrument to remove the surface treatment to provide a marking that may be retained on exterior surface 438. Surface treatment of exterior surface 438 may be realized using an abrasive treatment such as media blasting, sand blasting, sanding, and the like; a chemical treatment or coating such as one or more of: phosphating (Parkerizing), ferritic nitrocarberizing, anodizing, polymeric coating, epoxy coating, powder coating, and the like. Surface treatment to provide an enhanced grip and writing surface may also be realized using paint, other chemical treatment, chemical coating, chemical etching, tooling, or be effectuated in the manufacturing process of container portion 402.

Container portion 402 may allow for collection of both volatile chemical vapor samples and nonvolatile chemical samples, solids, liquids, and gases. Tamper-resistant chemical sampling apparatus 400 may also be adapted to collect and retain samples such as biological, isotopic, radiological, fissile, and the like. For example, an interior of container portion 402 may be operatively connected to calibrated orifice 430.

Figure 7:
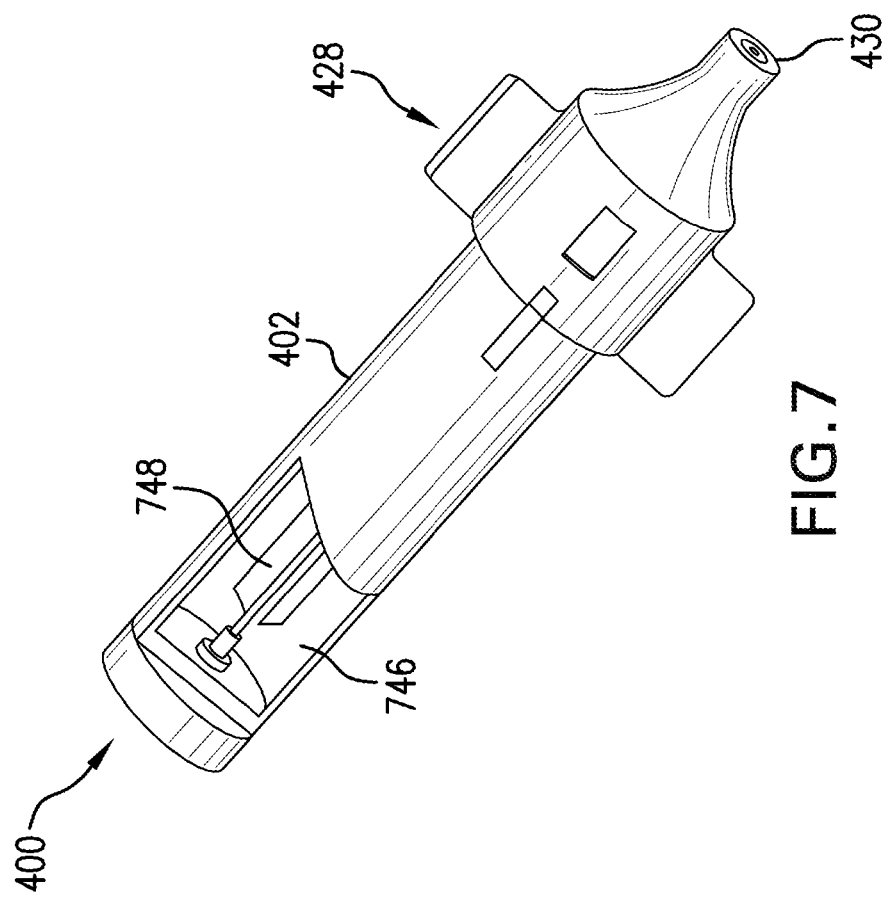
FIG. 7 illustrates an example tamper-resistant chemical sampling system.

With reference to FIG. 7, interior 746 of container portion 402 may be connected to calibrated orifice 430 by a chemical sample collector 748 that may assist in drawing a chemical sample through calibrated orifice 430, e.g., for collection and retention in interior 746 of container 402. For example, chemical sample collector 748 may include a solid-phase micro-extraction (SPME) fiber to assist in collecting a chemical sample. SPME fiber 748 may be coated with a liquid sorbent, polymer sorbent, a solid sorbent such as a zeolite, and the like. Such sorbent extracting phases may be employed to extract different types of volatile and nonvolatile chemical samples. For example, chemical sample collector 748 may include a sorbent tube. Sorbent tube 748 may include a sorbent such as activated charcoal, silica gel, an organic polymer, a resin, e.g., TENAX® resin (Sigma-Aldrich, St. Louis, Mo.), an organic polymer AMBERLITE® XAD resin (Dow, Midland Mich.), and the like.

Figure 8:
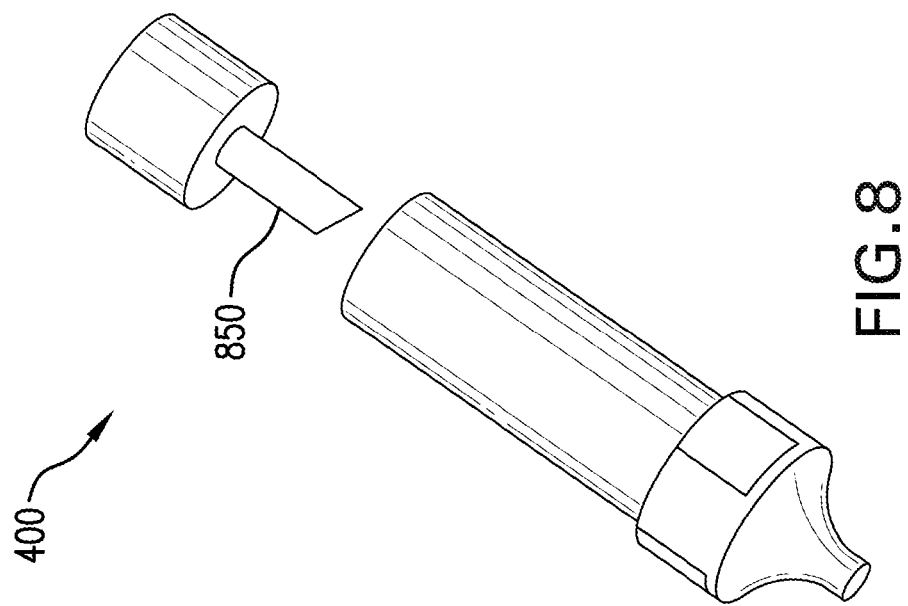
FIG. 8 illustrates an example tamper-resistant chemical sampling system.

Referring to FIG. 8, a chemical detector on a chip 850 may be used during collection of chemical samples. Chemical detector on a chip 850 may be used, e.g., to detect a presence of a chemical, e.g., a vapor. For example, chemical detector on a chip 850 may be used to detect chemical samples as a fraction of moles/mass in units such as parts per million (ppm), parts per billion (ppb), parts per trillion (ppt), and the like. Chemical detector on a chip 850 may provide a concentration of a target chemical in terms of weight by volume, such as mg/m$^3$. Chemical detector on a chip 850 may include one or more of memory and processor functionality such that different chemical profiles may be stored and cross referenced for detection and identification by chemical detector on a chip 850. Chemical detector on a chip 850 may detect a presence of one or more CWAs or TICs, as described below.

For example, chemical detector on a chip 850 may be configured to detect a presence of CWA vesicants. Vesicants (blister agents) may cause chemical burning and blistering, and may affect the skin, eyes, muscles, and the like. Vesicants may include, for example: phosgene oxime (CX); ethyldichloroarsine (ED); methyldichloroarsine (PD); lewisite (L); mustard gas (e.g., in variants H, HD, HT, HL, and HQ); nitrogen mustard (HN); and the like.

Chemical detector on a chip 850 may be configured to detect a presence of CWA nerve agents. Nerve agents may include organophosphates that may disrupt the nervous system, cause organ failure, and the like. Nerve agents may include, for example: tabun (GA); sarin (GB); soman (GD); cyclosarin (GF); V-Agents (e.g., variants such as EA-3148, VE, VG, VM, VRm, and VX); Novichok agents, and the like.

In another embodiment, chemical detector on a chip 850 may detect a presence of blood agents. Blood agents may be, for example, cyanide based, arsenic based, and the like, and may poison an organism's blood. Blood agents may be potentially lethal. Blood agents may appear both as CWAs and TICs. Blood agents may include, for example: hydrogen cyanide (AC); cyanogen ((CN)$_2$); cyanogen chloride (CK); cyanogen bromide (CNBr); arsine (AsH$_3$); vinyl arsine; phosgene (CG); sodium cyanide (NaCN); potassium cyanide (KCN); carbon monoxide (CO); and the like.

Chemical detector on a chip 850 may be configured to detect a presence of choking agents and/or lachrymators. Choking agents may affect an animal's ability to breathe. Lachrymators, e.g., tear gas, may cause tearing and may obstruct vision. Choking agents may be both CWAs and TICs. Choking agents and lachrymators may include, for example: chlorine gas (Cl$_2$); chloropicrin (PS); diphosgene (DP); phosgene (CG); disulfur decafluoride (S$_2$F$_{10}$); perfluoroisobutene (PFIB); acrolein; diphenylcyanoarsine; acid vapors; tear gas; capsacin and other biological irritants; and the like.

Chemical detector on a chip 850 may detect a presence of numerous toxic industrial chemicals (TICs) that may be improvised into a harmful chemical device. A non-limiting example of TICs may include one or more of: ammonia (NH$_3$), chlorine (Cl$_2$), fluorine (F$_2$), formaldehyde (CH$_2$O), hydrogen bromide (HBr), hydrogen chloride (HCl), hydrogen fluoride (HF), hydrogen cyanide (AC), nitric acid (HNO$_3$), nitrogen dioxide (NO$_2$), phosgene (CG), hydrogen sulfide (H$_2$S), sulfuric acid (H$_2$SO$_4$), sulfur dioxide (SO$_2$), and the like.

CWAs and TICs may be collected for analysis by chemical detector on a chip 850 and/or retained by chemical sample collector 748 within interior 746 of container portion 402, e.g., for later analysis in a laboratory environment. For example, tamper-resistant chemical sampling apparatus 400 may include both chemical detector on a chip 850 and chemical sample collector 748, e.g., for collecting and retaining a chemical sample within interior 746 of container portion 402.

Tamper-resistant chemical sampling apparatus 400 may be operable to collect and retain any of the above referenced CWAs and TICs. Because CWAs and TICs may be inhaled through the respiratory system, absorbed through skin and mucus membranes, and the like, chemical sampling may require users to wear protective garments when taking a chemical sample with tamper-resistant chemical sampling apparatus 400. Components of tamper-resistant chemical sampling apparatus 400 may be adapted such that users wearing protecting clothing may easily operate chemical sampling apparatus 400. For example, tamper-resistant chemical sampling apparatus 400 may be adapted for use with military Mission Orient Protective Posture (MOPP) protective gear. Protective gear may include use of one or more of protective masks, gas masks, goggles, shields, respirators (e.g., self-contained breathing apparatus (SCBA)), over-garments, Chemical, Biological, Radiological, Nuclear (CBRN) suits, Hazmat suits, gloves, other common chemical protection, and the like.

Container portion 402 may be insulated. All or portions of container portion 402 may be insulated to stabilize a temperature of interior 746 of container portion 402, e.g., to provide a temperature-stabilized collection and storage environment for a chemical sample. For example, temperature variations may affect the lifetime of chemical samples stored in container portion 402. For example, surface chemistry reactions may occur between a chemical sample and a sorbent during a collection of a chemical sample. Insulating container portion 402 may mitigate or eliminate temperature-varying effects during collection and retention a chemical sample. Insulating container portion 402 may also protect interior 746 of container 402 from extreme temperatures outside of container 402 to eliminate or mitigate temperature-varying effects that external extreme temperatures may cause during a collection and retention of a chemical sample. For example, container 402 may include as insulation one or more of: a mineral wool, a fiberglass, a glass wool, a cellulose, a rock wool, a polystyrene foam, a urethane foam, a vermiculite, a perlite, a cork, an aerogel or xerogel, an evacuated vacuum portion, a heat reflecting surface coating, and the like.

Tamper-resistant chemical sampling apparatus 400 may be smaller than previous generation chemical sampling apparatuses. In one embodiment, tamper-resistant chemical sampling apparatus 400 may be about or less than about than 8.5 inches (21.59 cm) in length, 1.75 inches (4.45 cm) in diameter, 0.5 pounds (1.1 kg), and the like. One or more tamper-resistant chemical sampling apparatuses 400 may easily be carried by and on a user.

With reference to FIG. 4, example tamper-resistant chemical sampling apparatus 400 may include one or more tamper-resistant components operable to resist tampering with a chemical sample. Such anti-tampering components may be unknown and/or invisible to a user taking a chemical sample.

For example, valve mechanism 428 may include one or more components to provide tamper-resistance to tamper-resistant chemical sampling apparatus 400. Valve mechanism 428 may be connected to one or more internal electrical components on tamper-resistant chemical sampling apparatus 400. Valve mechanism 428 may be connected to one or more devices that generates one or more DTG data, associated with a position of valve mechanism 428. For example, DTG data may be generated when valve mechanism 428 may be in an open position to collect a chemical sample. DTG data may include a prescribed format such as year, month, day, hour, minute, time zone, and the like. One or more DTG data may be generated by different events such as once during an opening of valve mechanism 428, once during a closing of valve mechanism 428, to indicate a time and date for each of a start and finish of a chemical sample, and the like. For example, one DTG data may be generated to indicate an elapsed time of a chemical sample. DTG data may be used, for example, to indicate chemical sampling tampering. For example, when DTG data indicates that valve mechanism 428 has remained in an open position for an extended period of time greater than a desired length of time, e.g., greater than about 5 seconds, or opened multiple times during a given interval, a suspicion of chemical sample tampering may be indicated.

Figure 5:
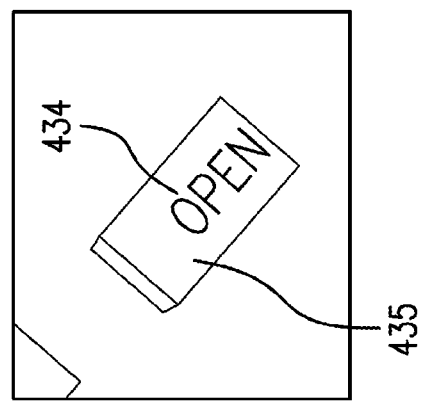
FIG. 5 illustrates an example tamper-resistant chemical sampling system.

Valve mechanism 428 may further include an indicator 434 to indicate a position of valve mechanism 428, e.g., to resist tampering with a collected chemical sample. With reference to FIG. 5, indicator 434 may be visible through indicator window 435. Indicator 434 may include text, graphics, colors, lights, audible cues, tactile cures, and the like to provide a user with an indication of a position of valve mechanism 428. For example, indicator 434 may include text such as "OPEN," "CLOSED," and "LOCKED" to indicate a corresponding position or status of valve mechanism 428. Further, for example, indicator 434 may use colors such as green and red to indicate an open and closed position of valve mechanism 428, respectively. Indicator 434 may use a picture or graphic to indicate a position of valve mechanism 428, a sampling status of tamper-resistant chemical sampling apparatus 400, such as using an "X" to indicate a closed position, an "O" to indicate an open position, and the like. Indicator 434 may include one or more lighting devices such as LEDs operable to display more than one color to indicate a sampling status of tamper-resistant chemical sampling apparatus 400 or position of valve mechanism 428. For example, an RGB LED may be used to display both red and green color lighting on a single LED to indicate different color status indicators. Indicator 434 may be sufficiently noticeable to a user wearing one or more articles of protective clothing such as masks, goggles, glasses, shields, and the like. For example, indicator 434 may be visible through indicator window 435 for certain positions of valve mechanism 428 (e.g., displaying "OPEN" when valve mechanism 428 is in an open position).

Referring again to FIG. 4, valve mechanism 428 may further include locking mechanism 436 to resist actuation of valve mechanism 428. Locking mechanism 436 may be a slide lock operable to resist rotation and actuation of valve mechanism 428. Slide lock 436 may be operable to engage one or more of slot 437 and indicator window 435 to resist rotation of valve mechanism 428. Slide lock 436 may be linearly actuated from an unlocked position to a locked position engaging slot 437 to resist actuation of valve mechanism 428. Locking mechanism 436 may include a compression spring (not shown) to vary a position of locking mechanism 436 relative to container portion 402 such that locking mechanism 436 may need to be depressed into container portion such that slot 437 does not catch on locking mechanism 436. Valve mechanism may be allowed to rotate once slot 437 has been disengaged from locking mechanism 436. A spring force may be used to automatically return locking mechanism 436 to an engaged position when slot 437 may be aligned relative to locking mechanism 436 such that locking mechanism 436 springs into place, engages slot 437, and resists rotation of valve mechanism

428. Locking mechanism 436 may be a simple device with relatively few components, such as a simple mechanical lock, or a complicated device that may interface with other components such as a processor and sensor configured to provide an electro-mechanical lock. Locking mechanism 436 may resist unauthorized or unwanted chemical sampling by controlling a position of valve mechanism 428. Locking mechanism 436 may allow for a single actuation of valve mechanism 428 and may provide a single chemical sample to be taken by tamper-resistant chemical sampling apparatus 400. Locking mechanism 436 may be disengaged by a user taking a chemical sample. For example, once engaged after taking a chemical sample, locking mechanism 436 may be capable of being disengaged by laboratory or other qualified personnel during analysis of a collected chemical sample. Locking mechanism 436 may be tailored specifically to an appropriate level of tamper-resistance depending on the intended use of tamper-resistant chemical sampling apparatus 400. For example, a substantial level of tamper resistance may be regarded as effectively "tamper-proof" for some applications. Locking mechanism 436 may be operatively connected with chemical detector on a chip 850 such that detection of specific chemicals may cause a locking of valve mechanism 428 relative to locking mechanism 436 after a chemical sample may be collected.

Valve mechanism 428 may be designed to assist in tamper-resistance of tamper-resistant chemical sampling apparatus 400. Valve mechanism 428 may include a twisting mechanism configured to cause a user to exert a significant amount of torque in order to change a position of valve mechanism 428. Valve mechanism 428 may use a linear actuation (e.g. push/pull in a direction of the longitudinal axis) to change a position of valve mechanism 428 prior to twisting valve mechanism 428 to collect a chemical sample. For example, a user may twist valve mechanism 428 a quarter turn to change a position of valve mechanism 428 from opened to closed and vice-versa. Valve mechanism 428 may include a mechanical device such as a torsion spring or coil spring to bias a rotational position of valve mechanism 428, e.g., to a preferred position such as closed. Valve mechanism 428 may cause a user to assert an additional rotational force to change a position of valve mechanism 428 before valve mechanism 428 may be opened to collect a chemical sample. Valve mechanism 428 may use one or more mechanical devices and directional forces to resist unwanted opening. For example, valve mechanism 428 may be biased with a coil spring to bias valve mechanism 428 on locking mechanism 436. For example, a user may be caused to exert enough force on valve mechanism 428 to disengage locking mechanism 436 and may be further caused to twist valve mechanism a quarter turn to an open position for chemical sampling. For example, absent any force from a user, valve mechanism 428 may automatically return to a closed and locked position after taking a chemical sample.

Valve mechanism 428 may include ease of use hardware such as raised tabs and fins 432 to assist a user in changing positions of valve mechanism 428 while wearing protective clothing and gear. For example, valve mechanism 428 may be a twist mechanism and valve mechanism 428 may employ hardware similar to one or more of: a fluted knob, a spoked knob, a winged knob, a tee knob, a skirted knob, a scalloped knob, an armed knob, a lobed knob, and the like, to assist a user with rotation of valve mechanism 428.

Tamper-resistant chemical sampling apparatus 400 may also include GPS device 440 to assist in tamper-resistance. As used herein, GPS device need not be limited to those navigation devices operable to receive GPS satellite signals from satellites operated by the U.S. Air Force Space Command (AFSPC). For example, GPS device 440 may refer to any space-based satellite navigation system, or terrestrial navigation systems, including but not limited to: GPS generally, GPS Block IIA, GPS Block IIF, GPS Block IIIA, GLONASS, GNSS, IRNSS, BDS, other regional satellite navigation systems, VOR, RDF, GPS2SMS, MLAT, and the like. GPS device 440 may be operable to receive a GPS satellite signal to provide a global coordinate position to indicate a collection location, date, and collection time of a chemical sample. GPS device 440 may be operable to acquire GPS signals from GPS satellites and generate a global coordinate of a location of a chemical sample based on GPS signals from GPS satellites. For example, a global coordinate position may be automatically generated by GPS device 440 during a collection of a chemical sample. For example, GPS device 440 may be operatively connected with valve mechanism 428 such that a global coordinate may be automatically generated during actuation of valve mechanism 428. Further, for example, when a GPS signal between GPS device 440 and GPS satellite cannot be established, GPS device 440 may automatically poll one or more GPS satellites at regular or intermittent intervals until a GPS satellite signal may be received and a global coordinate may be generated. GPS device 440 may be operable to generate one or more DTG data associated with one or more of: collection time of a chemical sample; collection duration of chemical sample; acquisition of global coordinate associated with a location of a chemical sample; attempts at establishing a global coordinate associated with a location of a chemical sample; error codes; tampering attempts; transfer of data from tamper-resistant chemical sampling apparatus 400 to an external device; and like events. GPS device 440 may help to positively correlate an alleged location of a CWA and TIC event to a chemical sample location. For example, a chemical weapons attack may be alleged at one location, but a chemical sample showing use of CWAs may have been generated in a laboratory for propaganda purposes to sway public opinion or prompt foreign military intervention. GPS device 440 may ensure that a chemical sample location matches a location of an alleged use of CWAs and TICs.

Figure 6:
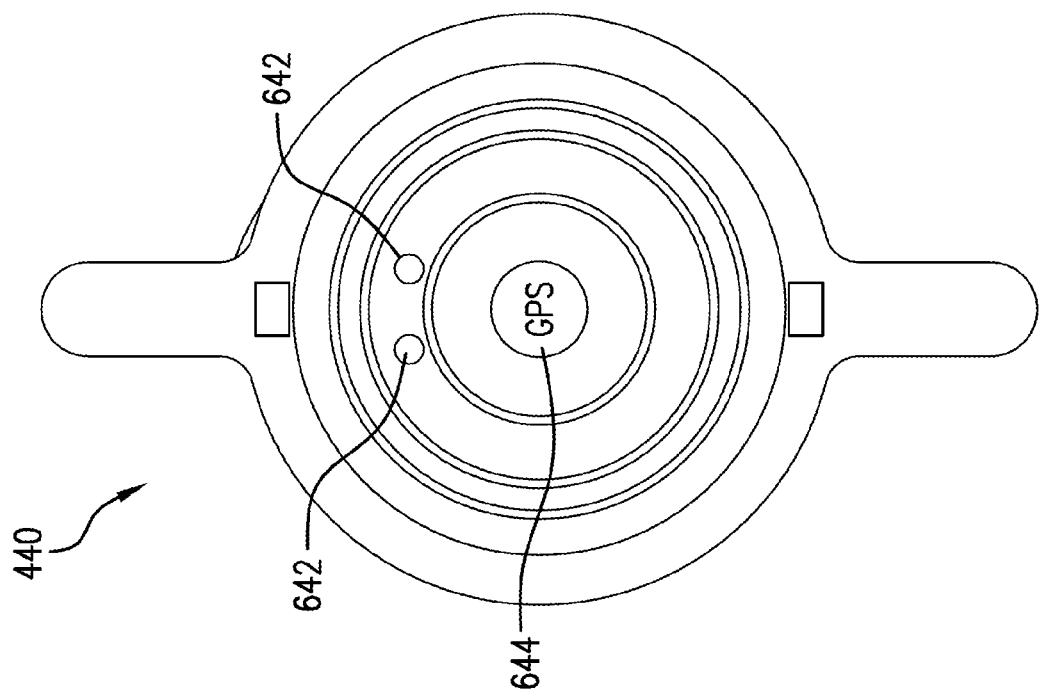
FIG. 6 illustrates an example tamper-resistant chemical sampling system.

Referring now to FIG. 6, an example GPS device 440 is illustrated. GPS device 440 may include indicator lights 642 to indicate a functionality of GPS device 440. Indicator lights 642 may use different indicators such as blinking lights, continuous lights, and lights of different colors to indicate the functionality of GPS device 440. For example, lights 642 may be red if no GPS signal has been acquired, and green if a GPS signal has been acquired. Lights 642 may blink if no GPS signal has been acquired and may, for example, remain continuously lit once a GPS signal has been acquired. Lights 642 may be, for example, an LED type light operable to output one or more colors. GPS device 440 may also include functionality to provide for manual acquisition of a GPS signal. For example, GPS button 644 may be provided to provide manual acquisition of a GPS signal. For example, a user may press GPS button 644 after taking a chemical sample to establish a global coordinate for a chemical sample location. If a global coordinate is not automatically acquired from a satellite signal by GPS device 440, indicator lights 642 may prompt a user to repeatedly push GPS button 644 until a global coordinate data may be established. For example, a chemical sample may be taken indoors and GPS device 440 may be prevented from receiving GPS satellite signals to establish global coordinate data related to a chemical sample location. For example, lights 642 may indicate that global coordinate data has not been generated, and may cause a user to move to another location to receive a GPS satellite signal. A user may then manually attempt to establish a connection between GPS device 440 and a GPS satellite by pressing GPS button 644. Accordingly, global coordinate data relatively close to a chemical sample location (i.e. immediately outdoors from an indoor sample location) may not raise tampering suspicion. By contrast, in some examples, a global coordinate data relatively attenuated from a collection location and collection time of an alleged chemical sample may raise a suspicion of chemical sample tampering.

Figure 9:
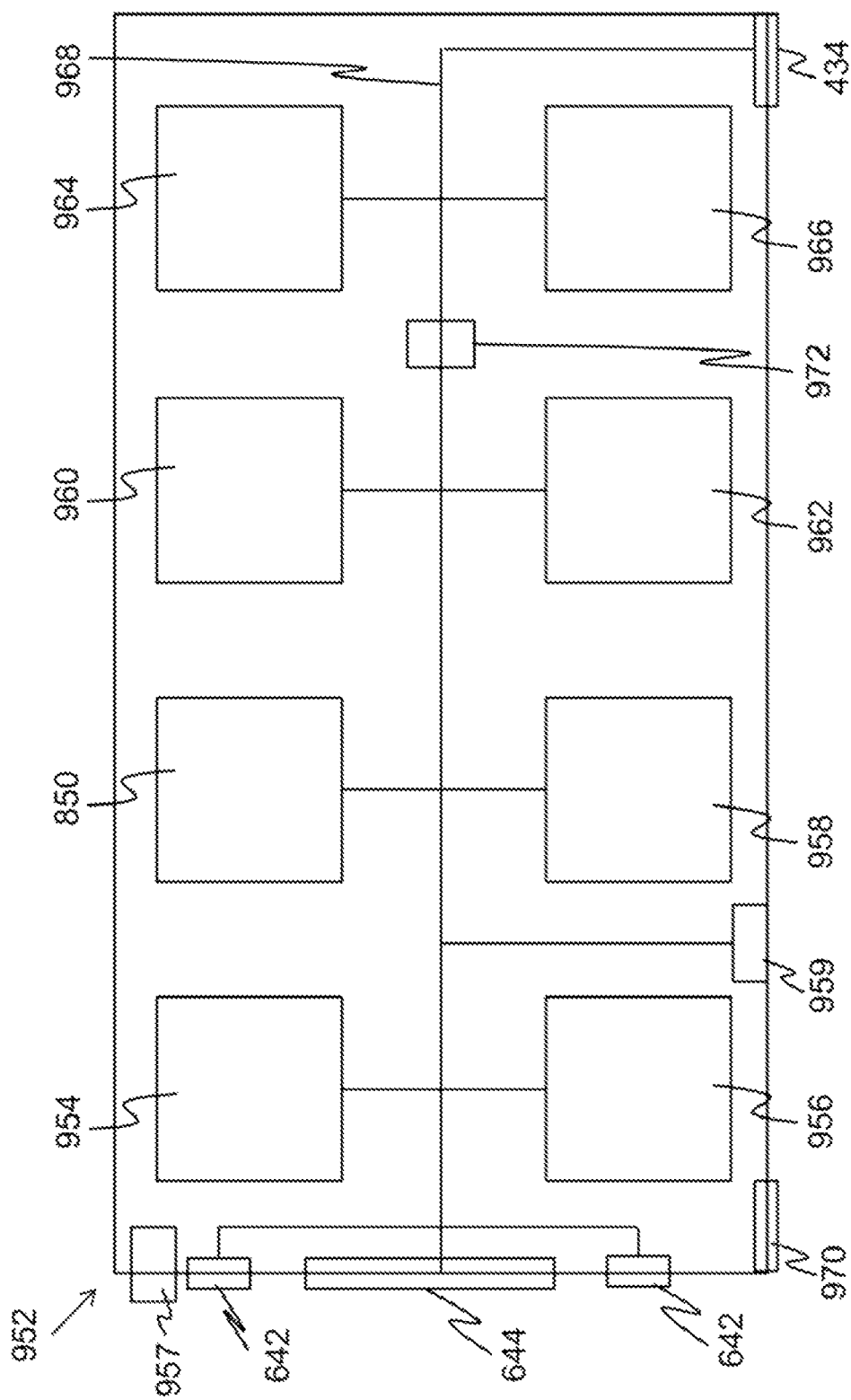
FIG. 9 illustrates an electronic schematic of an example tamper-resistant chemical sampling system.

Referring to FIG. 9, an example electronic schematic 952 of internal electronic components of tamper-resistant chemical sampling apparatus 400 is illustrated. Tamper-resistant chemical sampling apparatus 400 may include electronic components such as GPS receiver 954, transmitting/receiving device 956, chemical detector on a chip 850, one or more other sensors 958, processor 960, one or more memory devices 962, power source 964, timing chip 966, and the like. Electronic components may be operatively connected to one another using connection 968, e.g., to provide hardwired or wireless connection for electronic components. Connection 968 may use wires, printed circuit board (PCB) traces, a bus system such as $I^2C$, and other conductive pathways capable of transmitting electrical signals to interconnect electronic components. Electronic components may be interconnected separate assemblies, or one assembly. Electronic components may be potted or encapsulated to further minimize environmental effects and vibration on electronic components.

GPS receiver 954 may be operable to receive a GPS satellite signal and generate a global coordinate data in a format common to location and global positioning (e.g. decimal degrees (DD) of latitude and longitude, degrees, minutes, and seconds (DMS) of latitude and longitude, and the like). GPS receiver 954 may be further operable to attempt to acquire and receive a GPS satellite signal to generate global coordinate data when GPS button 644 on GPS device 440 is depressed. For example, GPS receiver 954 may be an integrated circuit that includes an antenna. Tamper-resistant chemical sampling apparatus 400 may, for example, use a dedicated antenna (not shown) for receiving a GPS satellite signal separate from GPS receiver 954.

Transmitting/receiving device 956 may be used to establish a wireless connection between tamper-resistant chemical sampling apparatus 400 and an external device such as a computer, or other hardware configured to wirelessly download data stored in one or more memory devices 962. Transmitting/receiving device 956 may include one or more of: a transmitting/receiving device, a transmitting device alone, or a receiving device alone. Transmitting/receiving device 956 may be, for example, a transmitter. Transmitting/receiving device 956 may be a receiver. Transmitting/receiving device 956 may be a transceiver. Transmitting/receiving device 956 may be a transponder. For example, transponder 956 may include a RFID transponder (RFID device) operable to wirelessly transmit data acquired during a chemical sample to an external device such as a laboratory computer. Use of RFID transponder 956 may resist data tampering by allowing read only access to data stored on tamper-resistant chemical sampling apparatus 400. RFID transponder 956 may be operable to both wirelessly transmit and receive radio signals. In Transmitting/receiving device 956 may include an integrated circuit that includes a built-in antenna. Tamper-resistant chemical sampling apparatus 400 may include a dedicated antenna (not shown) wholly separate from transmitting/receiving device 956, and may be used to wirelessly transmit data acquired during a chemical sample to an external device such as a laboratory computer.

Chemical detector on a chip 850 may interconnect with other electronic components of tamper-resistant chemical sampling apparatus 400 to provide enhanced operability. For example, detection of a specific chemical sample by chemical detector on a chip 850 may automatically trigger a DTG data event associated with a chemical sample collection time, and generation of a global coordinate associated with a collection location of the chemical sample. Chemical detector on a chip 850 may identify chemical components and store data related to one or more chemical components detected during a chemical sample. For example, chemical detector on a chip 850 may be able to identify a CWA in a mass/mole fraction in units of parts per billion, while also indicating a presence and amount of diesel exhaust in a chemical sample. Chemical detector on a chip 850 may compare a concentration of a CWA/TIC chemical sample against a known critical exposure concentration and may provide a user with an indication of critical exposure levels. Chemical detector on a chip 850 may include one or both of humidity and temperature sensing capabilities. Chemical detector on a chip 850 may record relative humidity and temperature data when detecting and recording chemical sample data.

For example, humidity and/or temperature may cause degradation over time of captured chemical samples, Humidity and/or temperature data may be used in combination with known decomposition rates of chemicals of interest to retroactively determine an original concentration of a chemical in a chemical sample at the time of sampling. For example, a sample may be taken and stored in the canister for a period of time at elevated temperature. The sample may degrade over time, leaving a lower concentration of the chemical by the time the sample canister may be returned for analysis. By knowing a decomposition rate of the chemical as a function of humidity and/or temperature, and modeling using the recorded humidity and/or temperature history, one may retroactively determine an original concentration of a chemical in a chemical sample at the time of sampling.

One or more other sensors 958 may be used to provide additional functionality to tamper-resistant chemical sampling apparatus 400. For example, sensor 958 may be an accelerometer or shock sensor to provide data related to one or more drops/falls of tamper-resistant chemical sampling apparatus 400. Sensor 958 may indicate a frequency and/or severity of drops to indicate possible negative effects on an integrity of a chemical sample. Sensor 958 may include a humidity sensor that records relative humidity at a collection time of a chemical sample. Such a relative humidity sensor may take a relative humidity sample of one or more of: a relative humidity (RH) in an environment outside tamper-resistant chemical sampling apparatus 400, an RH from inside tamper-resistant chemical sampling apparatus 400 where a chemical sample may be stored, or both. Sensor 958 may be a temperature sensor that records a temperature of one or more of: an environment outside tamper-resistant chemical sampling apparatus 400, inside tamper-resistant chemical sampling apparatus 400 where a chemical sample may be stored, or both. Other sensors may include sensors related to tampering detection, and position sensors to indicate a position of valve mechanism 428. For example, tampering detection sensor 958 may sense and store data if an attempt to collect more than one tamper-resistant chemical sampling occurs. Further, for example, position sensor 958 may sense a position of valve mechanism 428 and power up/power down other components based on a position of valve mechanism 428. Switch 970 may be used, e.g., as an on/off switch for providing power to electronic components. Switch 970 may be operatively connected to valve mechanism 428 such that a position of valve mechanism 428 may actuate switch 970. Switch 970 may be a cam switch that may be actuated by rotation of valve mechanism 428. Switch 970 may include a combination of valve mechanism 428 and locking mechanism 436. Valve mechanism 428 and locking mechanism 436 in combination may act as either a normally closed (NC) or normally open (NO) contact, such that disengaging valve mechanism 428 from locking mechanism 436, or engaging valve mechanism 428 to locking mechanism 436, may turn electronic components on or off depending on a position and contact of valve mechanism 428 relative to locking mechanism 436.

A processor 960 may be used to provide programmable functionality to tamper-resistant chemical sampling apparatus 400. Processor 960 may be a CPU. Processor 960 may be a microprocessor or microcontroller. Processor 960 may execute programs to perform functions related to chemical sampling and may coordinate interconnection between different electronic components of tamper-resistant chemical sampling apparatus 400. An instruction set or software may be stored on memory 962 and executed by processor 962 to perform one or more acts of a method for collecting a chemical sample.

Memory 962 may be used to store: programs to be executed by processor 960; chemical data profiles for chemical detector on a chip 850; and data generated during a chemical sampling, including, but not limited to: collection time of a chemical sample, GPS location of a chemical sample, acquisition time of GPS satellite signal, attempt time for each attempt of acquiring a GPS satellite signal, chemical on chip data related to a collected chemical sample, temperature history data, relative humidity history data, and the like. Memory 962 may be a non-volatile memory such as flash memory or a volatile memory such as RAM.

Power source 964 may be used to provide electrical energy to electronic components to operate electronic components during use of tamper-resistant chemical sampling apparatus 400. Power source may be a battery such as a primary, single use disposable battery, or rechargeable battery, with both battery types operable to convert stored chemical energy to electrical energy to power electronic components. Power source 964 may be, for example a rechargeable battery operable to be charged via inductive charging. Power source 964 may be, for example, a lithium coin cell 3V battery. Power source 964 may additionally include a crank dynamo that may be cranked to generate power that may be used to power tamper-resistant chemical sampling apparatus 400, stored in batteries 964, and the like. One or more converters 972 may be used to convert a voltage level from power source 964 to another voltage level for use by an individual electronic component. Converter 972 may be a buck converter, a boost converter, or a buck-boost converter. Converter 972 may be one of a rectifier, a converter, and an inverter operable to convert an AC power input to a DC power output (rectifier), a DC power input to a DC power output (converter), an AC power input to an AC power output (converter), or a DC power input to an AC power output (inverter).

A timing chip 966 may be used to provide DTG data independent of DTG data generated by GPS receiver 954. Timing chip 966 may serve as a backup to DTG data generated by GPS receiver 954. Timing chip 966 may be used to record DTG data for a specific function of tamper-resistant chemical sampling apparatus 400 (e.g., to record DTG data associated with a start, a stop, and a duration of a chemical sample). In one embodiment, timing chip 966 may be used as a primary hardware for indicating a collection time of a chemical sample.

External electrical components such as lights 642, button 644, power switch 970, and indicator 434 may also be interconnected to internal electronic components via connection 968. Additional components such as display 957 may be used to convey advanced information such as a CWA/TIC detected by detector on a chip 850, a concentration level of CWA/TIC, a time, a temperature, a humidity, a status, and the like. A vibration motor 959 may be used to provide a vibrational tactile feedback to a user when using tamper-resistant chemical sampling apparatus 400. A vibrational tactile feedback may be used to indicate status, error detection, successful operation, valve position, satellite signal acquisition (or lack thereof), and the like.

Tamper-resistant chemical sampling apparatus 400 may be individually packaged prior to chemical sampling use. Packaging (not shown) may be used to provide an indication that tamper-resistant chemical sampling apparatus 400 has no prior use. For example, tamper-resistant chemical sampling apparatus 400 may come in a sealed foil pouch, and a may be caused to open a sealed foil pouch prior to using tamper-resistant chemical sampling apparatus 400. Sealed foil pouch packaging may also be used as an additional custodial methodology and tamper-resistance during chemical sampling. For example, a user may need to physically break a seal on a packaging to remove tamper-resistant chemical sampling apparatus 400 from the packaging. After a chemical sampling, tamper-resistant chemical sampling apparatus 400 may be reinserted into the packaging and resealed with an adhesive, sticker, indicator, or other hardware to indicate a chemical sample has been made and that the packaging contains a used tamper-resistant chemical sampling apparatus 400 awaiting further chemical analysis. Packaging, such as a foil pouch, may also serve a decontamination barrier between tamper-resistant chemical sampling apparatus 400 and a user if an external surface of tamper-resistant chemical sampling apparatus 400 may have come into contact with one or more CWAs and TICs during chemical sampling.

Chemical samples collected by tamper-resistant chemical sampling apparatus 400 may provide for storage of a chemical sample for at least 120 hours without any effect on chemical samples. Tamper-resistant chemical sampling apparatus 400 may retain chemical samples such that an external relative humidity and external volatile organic compounds (VOCs) have no effect on chemical samples stored within tamper-resistant chemical sampling apparatus 400. Storage of tamper-resistant chemical sampling apparatus 400 containing a chemical sample in temperatures of −60° F. (−51° C.) to 160° F. (71° C.) may have no effect on retention and identification of chemical samples. Likewise tamper-resistant chemical sampling apparatus 400 may gather chemical samples at temperatures ranging from 0° F. (18° C.) to 100° F. (38° C.). Vibration, drops at heights of over about 6.5 feet (about 2 m), and decontamination of external surfaces of tamper-resistant chemical sampling apparatus 400 may all have no effect of chemical samples stored internally. CWA and TIC chemical samples may not leak, degrade, or affect performance of tamper-resistant chemical sampling apparatus 400 during transportation.

Chemical samples may be retained within tamper-resistant chemical sampling apparatus 400 until chemical samples may be analyzed by a laboratory or other analytical environment. Common chemical analytical techniques such as gas chromatography-mass spectrometry (GC-MS) may be used to analyze and identify chemical samples. Data associated with a collection and retention of chemical samples may be accessed by laboratories to verify correct chemical sampling techniques and chemical sampling location to further tamper-resist chemical samples collected and retained by tamper-resistant chemical sampling apparatus 400.

Tamper-resistant chemical sampling apparatus 400 may be adapted for use on any or all of platforms illustrated in FIGS. 2A, 2B, 3A, and 3B. Tamper-resistant chemical sampling apparatus 400 may be adapted for automatic and remote operation during use on platforms illustrated in FIGS. 2A, 2B, 3A, and 3B. For example, tamper-resistant chemical sampling apparatus 400 may not require an actuation of hardware 212 on vehicle mounting platform 206, but rather tamper-resistant chemical sampling apparatus may be controlled remotely (e.g., by wireless signal) to initiate collection of a chemical sample. In this way, a user need not exit a vehicle to collect a chemical sample using tamper-resistant chemical sampling apparatus 400 on vehicle mounting platform 206. Remote operation of tamper-resistant chemical sampling apparatus 400 on other platforms like building mounting platform 208 and robotic mounting platform 322 may also be possible. Size and shape of tamper-resistant chemical sampling apparatus 400 may allow for a reduction in size and materials used for mounting platforms 206, 208, and 322. For example, door 220 as illustrated in FIG. 2A may not be necessary due to tamper-resistance of tamper-resistant chemical sampling apparatus 400. Mounting platforms 206, 208, and 322 may hold an increased number of tamper-resistant chemical sampling apparatuses 400 compared to previous chemical sample apparatuses 100, thereby increasing a functionality of mounting platforms 206, 208, and 322. Chemical sampling apparatus 400 may combine with mounting platforms such as 206, 208, and 322 to provide a chemical sampling system.

Example

Testing of tamper-resistant chemical sampling apparatus 400 illustrated that CWA/TIC target analytes were detected under conditions approximating real life-sampling and handling. Trace level concentrations of varying CWA/TIC compositions were captured in tamper-resistant chemical sampling apparatuses 400. Subsequent laboratory analysis of collected chemical samples provided clear and regular identification of target analytes, thus proving the effectiveness of tamper-resistant chemical sampling apparatus 400 of collecting and maintaining a chemical sample. Testing used four nerve agents (Sarin GB, Tabun GA, Soman GD, and Cyclosarin GF), a blister agent (Distilled Mustard HD), and four TICS (Hydrogen Cyanide AC, Cyanogen Chloride CK, Hydrogen Sulfide WS, and Sulfur Dioxide SOD). The chemical samples were exposed to four different environmental conditions, and later tested to determine the effect of environment conditions on the viability of maintaining the chemical sample. Environmental conditions included: samples exposed to and collected from a relative humidity (RH) of 30%; samples exposed to and collected from an RH of 80%, samples exposed to and collected from an RH of 30% and stored for a minimum of 5 days at 100° C., and samples exposed to and collected from an environment with an additional 1% of diesel exhaust by volume.

The tamper-resistant chemical sampling apparatuses 400 were cleaned according to the Environmental Protection Agency (EPA) canister cleaning method used for the EPA TO15 analytical method for volatile organic chemical (VOC) analysis provided in the "Compendium of Methods for the Determination of Toxic Organic Compounds in Ambient Air—Second Edition" (EPA/625/R-96/010b, January 1999). The tamper-resistant chemical sampling apparatuses 400 were evacuated in preparation for sample collections. Air streams containing the chemicals of interest were created either by mixing gases purchased in cylinders, or by generating the required chemical vapors from solutions of the chemicals using a jet and plenum apparatus, and mixing the solutions of the chemicals with VOC-free air. An approximate concentration of each target chemical in each gas stream was verified by direct sampling and analysis of the gas stream. Three 400 cm$^3$ samples from each gas stream were collected in three different tamper-resistant chemical sampling apparatuses 400 for each test, e.g., 3 samples at 30% RH, 3 samples at 80% RH, 3 samples at 30% RH for storage at 100° C. for a minimum of 5 days, and 3 samples at 30% RH with 1% diesel exhaust added. The samples were analyzed using gas chromatography/mass spectrometry (GC/MS).

Check marks (✓) in Table 1 indicate consistent detection of the sample analyte at concentration levels below the critical exposure concentration. The critical exposure concentration was adopted from the 10 minute Critical Health Effect Levels as provided by the U.S. Army Public Health Command (USAPHC), Technical Guide (TG) 230, Environmental Health Risk Assessment and Chemical Exposure Guidelines for Deployed Military Personnel.

TABLE 1

Chemicals tested, and results of testing

| | | | Test Conditions | | | |
|---|---|---|---|---|---|---|
| Analyte Tested | Designation or Formula | Critical Exposure Concentration (mg/m$^3$) | Analyte Detected (30% RH) | Analyte Detected (80% RH) | Analyte Detected After Prolonged Storage at 100° C. (Days Stored) | Analyte Detected with Diesel Exhaust |
| Sarin | GB | 0.22 | ✓ | ✓ | ✓ (19) | ✓ |
| Tabun | GA | 0.22 | ✓ | ✓ | ✓ (7) | ✓ |
| Soman | GD | 0.089 | ✓ | ✓ | ✓ (5) | ✓ |

TABLE 1-continued

Chemicals tested, and results of testing

| Analyte Tested | Designation or Formula | Critical Exposure Concentration (mg/m$^3$) | Test Conditions | | | |
|---|---|---|---|---|---|---|
| | | | Analyte Detected (30% RH) | Analyte Detected (80% RH) | Analyte Detected After Prolonged Storage at 100° C. (Days Stored) | Analyte Detected with Diesel Exhaust |
| Cyclosarin | GF | 0.089 | ✓ | ✓ | ✓ (5) | ✓ |
| Distilled Mustard | HD | 2.5 | ✓ | ✓ | ✓ (7) | ✓ |
| Hydrogen Cyanide | AC | 30 | ✓ | ✓ | ✓ (6) | ✓ |
| Cyanogen Chloride | CK | 10 | ✓ | ✓ | ✓ (5) | ✓ |
| Hydrogen Sulfide | H$_2$S | 110 | ✓ | ✓ | ✓ (7) | ✓ |
| Sulfur Dioxide | SO$_2$ | 79 | ✓ | ✓ | ✓ (5) | ✓ |

Table 1 provides the findings of tests conducted with the test analytes. The ability of tamper-resistant chemical sampling apparatus 400 to collect and maintain the target analytes were verified using test conditions approximating real-life sampling and handling. CWAs/TICs of interest were introduced into tamper-resistant chemical sampling apparatuses 400, at low challenge concentrations, and were identified with confidence upon chemical analysis of chemical samples stored in tamper-resistant chemical sampling apparatuses 400. The challenge concentration for the chemicals were lower than the critical exposure concentrations listed in Table 1, and all of the target analytes were regularly and clearly identified for each of the four sets of test conditions. Sarin was allowed to remain in three tamper-resistant chemical sampling apparatuses 400 at 30% RH and 100° C. for 19 days and was still detected in samples recovered from all three tamper-resistant chemical sampling apparatuses 400. While the diesel exhaust gas mixture, which contained sulfur dioxide (SO$_2$), added to the presence of sulfur dioxide (SO$_2$) in the interferent containing samples, the presence of sulfur dioxide (SO$_2$) did not interfere with the detection of the other target analytes in interferent containing samples. Accordingly, the testing validated the performance of the tamper-resistant chemical sampling apparatus 400 for the collection of the CWAs/TICs listed.

FIG. 10 illustrates an example method 1000 for tamper-resistant chemical sampling. In one embodiment, method 1000 includes: removing a tamper-resistant chemical sampling apparatus from a protective packaging (1001); turning a twist mechanism on a tamper-resistant chemical sampling apparatus to an open position to allow a chemical sample to be collected into a tamper-resistant chemical sampling apparatus through a calibrated orifice (1003); leaving a twist mechanism in an open position for a period of time, e.g., about or at least about 5 seconds, to collect a chemical sample through a calibrated orifice into a tamper-resistant chemical sampling apparatus (1005); turning a twist mechanism on a tamper-resistant chemical sampling apparatus to a closed position after collecting a chemical sample to retain a chemical sample within a tamper-resistant chemical sampling apparatus (1007); locking a twist mechanism into a locked position to resist turning of a twist mechanism (1009); examining a GPS indicator light after closing and locking a twist mechanism to determine successful acquisition of a GPS satellite signal, and recordation of a GPS coordinate (1011); and placing tamper-resistant chemical sampling apparatus back into a packaging and sealing packaging for transport of tamper-resistant chemical sampling apparatus to a laboratory or other analysis facility (1013).

If in examining a GPS indicator light to determine acquisition of a GPS satellite signal and recordation of a GPS coordinate, a user determines acquisition and recordation were not successful, a user may manually actuate a GPS switch to acquire a GPS satellite signal to record GPS coordinate data associated with a collection location of a chemical sample.

Figure 11:
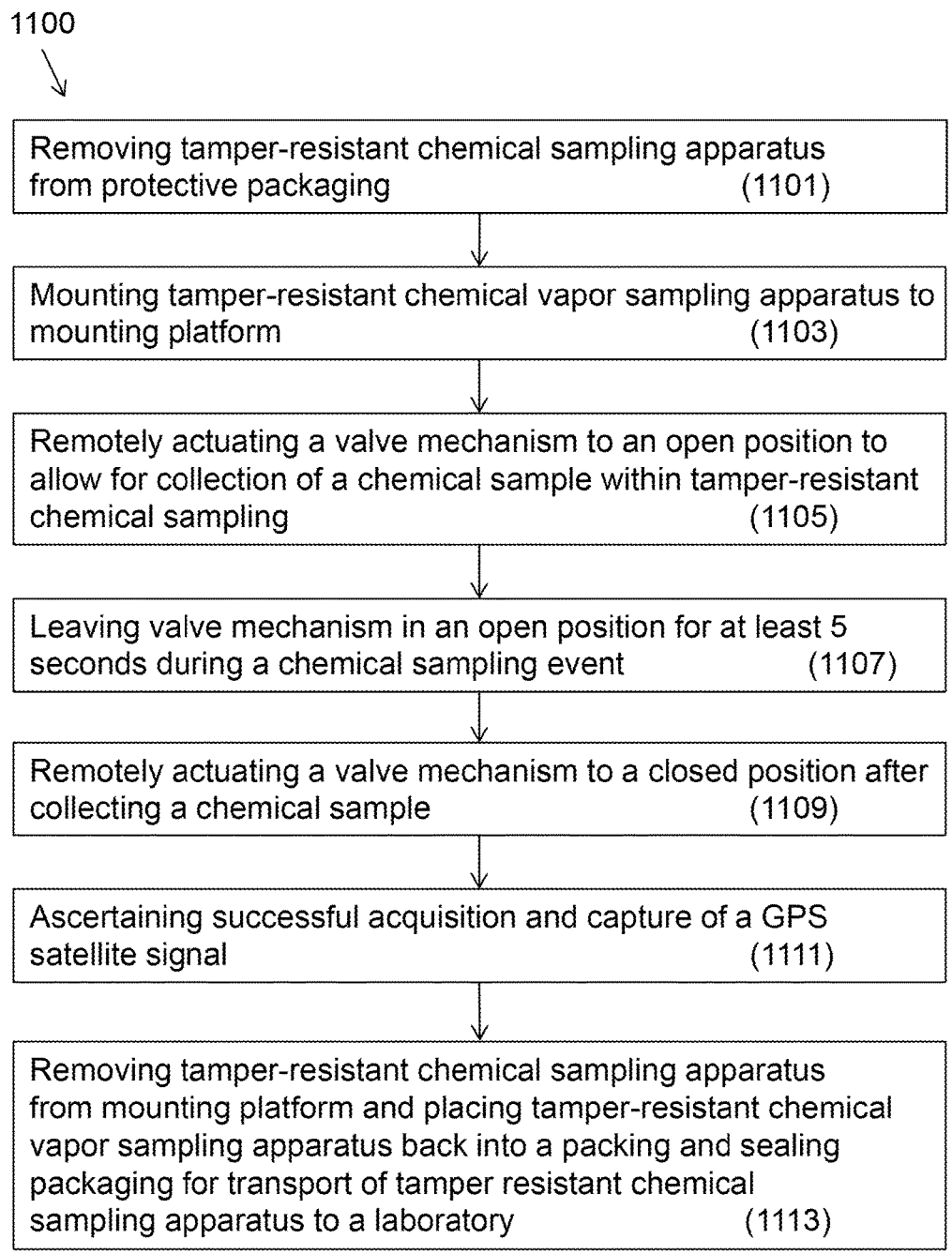
FIG. 11 is a flow chart of an example method for tamper-resistant chemical sampling.

FIG. 11 illustrates an example method 1100 for tamper-resistant chemical sampling. In one embodiment, method 1100 includes: removing a tamper-resistant chemical sampling apparatus for a protective packaging (1101); mounting tamper-resistant chemical sampling apparatus to a mounting platform (1103); remotely actuating a valve mechanism on a tamper-resistant chemical sampling apparatus to an open position to allow a chemical sample to be collected into a tamper-resistant chemical sampling apparatus through a calibrated orifice (1105); leaving a valve mechanism in an open position for a period of time, e.g., about or at least about 5 seconds, effective to collect a chemical sample through a calibrated orifice into a tamper-resistant chemical sampling apparatus (1107); remotely actuating a valve mechanism on a tamper-resistant chemical sampling apparatus to a closed position after collecting a chemical sample to retain a chemical sample within a tamper-resistant chemical sampling apparatus (1109); ascertaining successful acquisition and capture of a GPS satellite signal (1111); removing tamper-resistant chemical sampling apparatus from mounting platform and placing tamper-resistant chemical sampling apparatus back into a packaging and sealing packaging for transport of tamper-resistant chemical sampling apparatus to a laboratory or other analysis facility (1113).

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

As used in the specification and the claims, the singular forms "a," "an," and "the" include the plural. To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11.

What is claimed:

1. A tamper-resistant system for chemical sampling, comprising:
   a container operable to collect and retain a chemical sample; and
   a tamper-resistant mechanism, the tamper-resistant mechanism being operable to:
      disengage at a first chemical vapor sampling to allow for a collection of a chemical vapor sample after disengagement;
      record one or more of: a date, a time, and a location of the chemical sample during the collection of the chemical sample; and
      re-engage and lock to resist subsequent chemical samples after the first chemical sampling, wherein the tamper-resistant mechanism further comprises a slide lock and a twist mechanism, the slide lock being configured to actuate to allow rotation of the twist mechanism, and the twist mechanism being configured to rotate to disengage the slide lock to allow the chemical sample to be drawn through a calibrated orifice into an interior of the container, wherein the calibrated orifice is on the twist mechanism.

2. The system of claim 1, the container comprising a durable material, the durable material being:
   non-reactive with one or more of a chemical warfare agent and a toxic industrial chemical; and
   capable of retaining a chemical sample within the container after a drop shock sustained by dropping the container from a height of at least about 2 meters onto a concrete surface.

3. The system of claim 1, one or more of:
   an interior of the container comprising a passivated stainless steel configured to collect the chemical sample including one or more of: a volatile chemical vapor sample, and a non-volatile chemical sample; and
   an exterior of the container comprising a surface treatment, the surface treatment being one or more of:
      formed on the exterior of the container by one or more of: abrasion, chemical reaction; and coating, and
      operable to accept and retain one or more of: an inked-based marking, a pigment based marking, a paint-based marking, graphite or charcoal-based marking, a wax-based marking, an abrasive-based marking, and an impact based marking.

4. The system of claim 1, comprising within the container a chemical sample collector comprising one or more of:
   a solid-phase micro-extraction (SPME), the SPME comprising a fiber coated with an extracting phase for collecting the chemical sample, the extracting phase comprising one or more of: a sorbent liquid, a sorbent solid, and a sorbent polymer; and
   a sorbent tube, the sorbent tube comprising one or more of: an activated charcoal, a silica gel, and a porous polymer resin.

5. The system of claim 1, comprising a chemical detector on a chip within the container, the chemical detector on a chip being configured to detect one or more of a presence and a concentration of a chemical.

6. The system of claim 5, the chemical detected by the chemical detector on a chip comprising one or more of:
   a vesicant, the vesicant comprising one or more of: phosgene oxime (CX); ethyldichloroarsine (ED); methyldichloroarsine (MD); phenyldichloroarsine (PD); lewisite (L); mustard gas (HD); and nitrogen mustard (HN);
   a nerve agent, the nerve agent comprising or more of: tabun (GA); sarin (GB); soman (GD); cyclosarin (GF); a V-Agent; and a Novichok agent;
   a blood agent, the blood agent comprising one or more of: cyanogen chloride (CK) and hydrogen cyanide (AC);
   a lachrymator;
   a choking agent, the choking agent comprising one or more of: chlorine gas (Cl2); chloropicrin (PS); diphosgene (DP); phosgene (CG); disulfur decafluoride; perfluoroisobutene; acrolein; and diphenylcyanoarsine; and
   a toxic industrial chemical (TIC), the TIC comprising one or more of: ammonia ($NH_3$), chlorine ($Cl_2$), fluorine ($F_2$), formaldehyde ($CH_2O$), hydrogen bromide (HBr), hydrogen chloride (HCl), hydrogen fluoride (HF), hydrogen cyanide (AC), nitric acid ($HNO_3$), nitrogen dioxide ($NO_2$), phosgene (CG), hydrogen sulfide ($H_2S$), sulfuric acid ($H_2SO_4$), and sulfur dioxide ($SO_2$).

7. The system of claim 1, the tamper-resistant mechanism further comprising an indicator configured to indicate a status of one or more of the disengagement and the chemical sampling, the indicator comprising one or more of: a text-based status indicator, a color-based status indicator, a tactile status indicator, an audible status indicator, and a graphic-based status indicator.

8. The system of claim 1, the tamper-resistant mechanism further comprising a timing chip operable to automatically assign and store a first date-time group (DTG) upon disengagement of the tamper-resistant mechanism.

9. The system of claim 8, the system further comprising a global positioning system (GPS) operatively connected to the tamper resistant mechanism, the GPS being configured to:
receive a GPS satellite signal and record a global coordinate for a location of the chemical sample; and
record a second DTG upon recording the global coordinate.

10. The system of claim 9, wherein with respect to the GPS, one or more of:
the system being configured to automatically: record a first DTG associated with a first time upon collection of the chemical sample; and record the second DTG associated with a second time upon recording the global coordinate;
the GPS further comprising a GPS button configured to acquire or attempt to acquire the GPS satellite signal, or attempts to acquire the GPS satellite signal, to assign and record the global coordinate associated with the chemical sample, and wherein the global coordinate and the second DTG are automatically assigned and recorded when the GPS acquires the GPS satellite signal;
the GPS further comprising one or more indicator lights configured to indicate one or more of acquisition of the GPS satellite signal and recordation of the global coordinate; and
the GPS being configured to automatically attempt to acquire the GPS satellite signal at a fixed or irregular interval; and the tamper resistant chemical sampling system being configured to record one or more attempt DTGs for each unsuccessful GPS satellite signal acquisition attempt.

11. The system of claim 1, the system further comprising a memory, the memory being operable to store data related to one or more of: a chemical data associated with a chemical detection by a chemical detector on chip; a first DTG data associated with a chemical sample collection time; GPS and global coordinate data associated with a collection location of the chemical sample; a second DTG associated with an acquisition of a GPS satellite signal by a GPS and a recordation of the global coordinate data; one or more attempt DTGs associated with each of one or more attempts by the GPS to acquire the GPS satellite signal, and a temperature data associated with a temperature within the container.

12. The system of claim 11, the system further comprising a tamper-resistant data transfer device for transferring data stored on the memory to a data receiving device external to the container.

13. The system of claim 12, the tamper-resistant data transfer device comprising a radio frequency identification (RFID) device.

14. The system of claim 1, the system being further operable to collect and retain one or more of: a biological sample, an isotope, a radiological sample, and a fissile material.

15. A tamper-resistant apparatus for chemical sampling, the apparatus comprising:
(1) a stainless steel canister configured to retain a chemical sample, the stainless steel canister comprising an outer surface and an inner surface:
the outer surface comprising a surface treatment configured to provide one or more of: an increased friction between the outer surface and another surface, a markable surface configured to accept and retain a marking; and
the inner surface being passivated to reduce a chemical reactivity between the stainless steel canister and the chemical sample;
(2) a tamper-resistant mechanism, the tamper-resistant mechanism being operable to collect, retain, and protect the chemical sample from tampering, the tamper-resistant mechanism comprising:
a slide lock, the slide lock operable to resist rotation of a twist mechanism;
a twist mechanism the twist mechanism being operable to rotate from a closed position to an open position effective to allow the chemical sample to pass into an interior of the stainless steel canister through a calibrated orifice, wherein the calibrated orifice is on the twist mechanism;
an electronic device operable to generate a first DTG data associated with a collection time of the chemical sample;
a GPS device operable to:
acquire a GPS satellite signal and generate a global coordinate data associated with a location of the chemical sample;
assign and record a second DTG data associated with an acquisition time of the GPS satellite signal by the GPS; and
record one or more attempt DTG data associated with a time for each attempt by the GPS device to acquire the GPS satellite signal;
a memory operable to store one or more of: the first DTG data, the global coordinate data, the second DTG data, the attempt DTG data, chemical data associated with a chemical sample detected by a chemical detector on a chip, temperature data, and a fault code;
an RFID device operable to wirelessly transfer one or more data stored on the memory to a data receiving device external to the container; and
(3) an extractor operatively connected to the calibrated orifice and operable to extract one or more analytes from the chemical sample, the extractor comprising gone or more of: a SPME fiber, a glass tube, a chemical detector on chip, a polymer, and a sorbent.

16. The apparatus of claim 15, one or more of:
the twist mechanism further comprising one or more of: a fluted knob, a spoked knob, a scalloped knob, a winged knob, a tee knob, a skirted knob, an armed knob, and a lobed knob; and
the GPS device further comprising a switch, the switch being operable upon actuation to cause one or more of:

acquiring of the GPS satellite signal, attempting to acquire the GPS satellite signal, and recording a global coordinate data.

17. The apparatus of claim 15, one or more of:

the tamper-resistant mechanism further comprising a visual indicator configured to indicate an open and closed position of the twist mechanism; and the GPS devices further comprising one or more indicator lights configured to indicate one or more of: operation of the GPS device, acquisition of the GPS satellite signal by the GPS device, and recordation of the global coordinate data.

\* \* \* \* \*